United States Patent [19]

Desbois et al.

[11] Patent Number: 4,465,842
[45] Date of Patent: Aug. 14, 1984

[54] PREPARATION OF N-BENZYLIMIDES

[75] Inventors: Michel Desbois, Rillieux; Michel Reppelin, Collonges-au-Mont-d'Or, both of France

[73] Assignee: Rhone-Poulenc Specialites Chimiques, Courbevoie, France

[21] Appl. No.: 378,223

[22] Filed: May 14, 1982

[30] Foreign Application Priority Data

May 15, 1981 [FR] France .................................. 81 09698

[51] Int. Cl.³ .................... C07D 209/48; C07D 207/12
[52] U.S. Cl. ...................................... 548/473; 546/219; 548/480; 548/545
[58] Field of Search ........................ 548/473, 480, 545; 546/219

[56] References Cited

FOREIGN PATENT DOCUMENTS 2526652 12/1976 Fed. Rep. of Germany ...... 548/473

OTHER PUBLICATIONS

Houben-Weyl, Methods of Organic Chemistry, vol. XI/1, pp. 795-805, (1957).

*Primary Examiner*—Donald G. Daus
*Assistant Examiner*—M. C. Eakin
*Attorney, Agent, or Firm*—Burns, Doane, Swecker & Mathis

[57] ABSTRACT

The N-benzylimides having the structural formula:

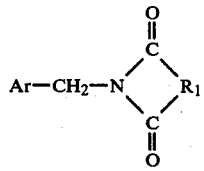

(I)

wherein Ar comprises a benzene radical and $R_1$ is an aliphatic or aromatic hydrocarbon, are prepared in good yield by reacting a compound having the structural formula:

ArH  (II)

with a compound having the structural formula:

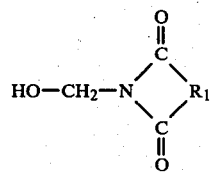

(III)

in the presence of hydrofluoric acid.

10 Claims, No Drawings

PREPARATION OF N-BENZYLIMIDES

BACKGROUND OF THE INVENTION

1. Field of the Invention

The present invention relates to the preparation of N-benzylimides, and, more especially, to the preparation of those substituted or unsubstituted N-benzylimides having the structural formula:

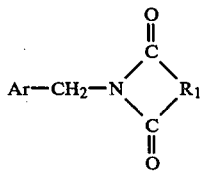
(I)

wherein Ar is a benzene radical and $R_1$ is an aliphatic or aromatic hydrocarbon.

By "benzene" radical as utilized herein, there is intended a substituted or unsubstituted phenyl moiety, as hereinafter more fully set forth.

2. Description of the Prior Art

It is known to this art, from West German Pat. No. 2,526,652, to react an optionally substituted trifluoromethylbenzene with N-hydroxymethylphthalimide to yield N—trifluoromethylbenzyl)phthalimides. This reaction is carried out by heating the two reactants to a temperature of about 50° C. for several hours, in sulfuric acid.

Nonetheless, the use of sulfuric acid on an industrial scale is fraught with certain disadvantages. In effect, the product of the reaction is dissolved in the sulfuric acid; furthermore, the water formed during the reaction remains present; and the distillation of the water and $H_2SO_4$ is virtually impossible because it requires levels of temperature which are incompatible with the stability of the desired products. It is thus necessary either to dilute the reaction mixture with water to enable extraction with an organic solvent, or to conduct such extraction in a concentrated sulfuric acid medium, which latter is quite difficult and complicated. Furthermore, in the case of fluorine compounds (as is the aforenoted West German patent), the presence of the $H_2SO_4$ gives rise to certain objectionable defluoration reactions which are detrimental both economically and technically.

Finally, the oxidizing and sulfonating properties of sulfuric acid give rise to the formation of numerous by-products.

SUMMARY OF THE INVENTION

Accordingly, a major object of the present invention is the provision of an improved process for the preparation of the substituted or unsubstituted N-benzylimides in economically acceptable yields, which improved process is conspicuously devoid of those disadvantages and drawbacks attendant N-benzylimide production in a sulfuric acid reaction medium.

Briefly, the present invention features a process for the preparation of substituted or unsubstituted N-benzylimides by reacting a compound having the formula:

ArH (II)

wherein Ar is a benzene radical, with a compound having the formula:

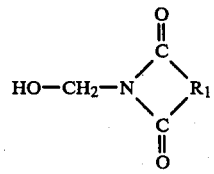
(III)

wherein $R_1$ is an aliphatic or aromatic hydrocarbon having from 1 to 12 carbon atoms, in the presence of hydrofluoric acid.

DETAILED DESCRIPTION OF THE INVENTION

More particularly according to the present invention, the hydrofluoric acid employed is preferably anhydrous hydrofluoric acid.

And it is also preferred to employ an aqueous hydrofluoric acid having a concentration in excess of 90%.

In a preferred embodiment of the process according to this invention, Ar is a phenyl radical in Formula (II), substituted with at least one of the substituents, F, Cl, Br, CN, $NO_2$, $NH_2$, CHO, COOH, COR or COOR, wherein R is an alkyl radical having from 1 to 6 carbon atoms, or an alkyl or alkoxy radical having from 1 to 6 carbon atoms, or a phenyl or phenoxy radical, or a radical $CF_3$, $SCF_3$ or $OCF_3$.

The process according to the invention is especially well adapted for reaction of compounds having the Formula (III) wherein $R_1$ is $-CH_2-CH_2-$, $-CH_2-CH_2-CH_2-$ or

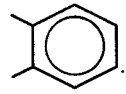

Preferably, an amount of hydrofluoric acid is used such that the molar ratio of HF to the reactant having the Formula (II) ranges from about 5 to about 50.

The reactants having the formulae (II) and (III) are preferably employed in amounts such that the molar ratio of (II) to (III) ranges from about 0.5 to about 2.

The process according to the invention is, moreover, advantageously carried out at a temperature ranging from about 0° C. to about 100° C.

When the temperature is higher than the boiling point of HF (20° C.), the reaction is carried out in a closed reactor under autogenous pressure. Contrariwise, it is preferred to carry out the reaction under atmospheric pressure, albeit pressures either higher or lower than atmospheric remain within the scope of the invention.

The reaction times typically range from a few minutes to about 20 hours.

The separation of the products of reaction may be effected by any technique conventional to this art, and in particular, by pouring the crude reaction mixture onto ice and extracting same with an organic solvent extractant, or by distillation of the HF (flash distillation, for example).

Exemplary of the reactants having the Formula (II), the following are representative: trifluoromethylbenzene, fluorobenzene, trifluoromethoxybenzene, trifluoromethylthiobenzene, chlorobenzene, phenol, anisole, veratrol, guaiacol, toluene, nitrobenzene, diphenyl oxide, o-cresol, m-cresol, p-cresol, ethylbenzene, benzonitrile, aniline, acetophenone, benzoic acid, di- and trichlorobenzenes, the chloronitrobenzenes, the chlorotoluenes, the nitrotoluenes, biphenyl, the chlorotrifluoromethylbenzenes, the bromotrifluoromethylbenzenes, the fluorotoluenes, the chlorotrifluoromethoxybenzenes, and meta-bis-trifluoromethylbenzene.

And representative of the reactants having the Formula (III) are: N-hydroxymethylsuccinimide, N-hydroxymethylglutarimide, N-hydroxymethylphthalimide, N-hydroxymethyl-2-methylsuccinimide, N-hydroxymethyl-2,3-dimethylsuccinimide, N-hydroxymethyl-2-phenylsuccinimide, and N-hydroxymethyl-2,4-dimethylglutarimide.

Thus, representative substituted or unsubstituted N-benzylimides having the Formula (I) which are facilely prepared according to the invention are: N-(-meta-trifluoromethylbenzyl)phthalimide, N-(-meta-bis-trifluoromethylbenzyl)phthalimide, N-(-2,4-dichlorobenzyl)phthalimide, N-ortho- and N-(-para-trifluoromethoxybenzyl)phthalimide, N-ortho- and N-(-para-fluorobenzyl)phthalimide, and N-ortho- and N-(-para-trifluoromethylthiobenzyl)phthalimide.

The corresponding derivatives of succinimide and glutarimide are also representative.

The product compounds having the Formula (I) are useful intermediates for the synthesis of a wide variety of active agents having pharmaceutical or phytosanitary activity.

For example, same may be treated with hydrazine, or hydrolyzed, to yield the amines Ar—CH$_2$—NH$_2$ (compare in this respect, the West German Pat. No. 2,526,652).

In order to further illustrate the present invention and the advantages thereof, the following specific examples are given, it being understood that same are intended only as illustrative and in nowise limitative.

EXAMPLE 1

Preparation of N—meta-trifluoromethylbenzyl)phthalimide

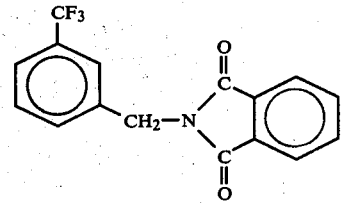

Into a stainless steel reactor, 90 g (4.5 moles) of anhydrous HF were introduced and cooled to about 0° C. Next, 17.7 g (0.1 mole) hydroxymethylphthalimide were slowly introduced, the temperature was maintained from 0° to 5° C. Then, 17 g (0.116 mole) trifluoromethylbenzene were dropped therein. The reactor was closed and heated to 50° C. under agitation for 20 hours. It was then cooled to 0° to 5° C.

The reaction mixture was poured onto 200 g of ice and the organic phase was extracted with methylene chloride (5×100 cm$^3$). The organic phase was then washed with demineralized water until a wash water having a pH between 5 and 6 resulted. Same was dried and evaporated under reduced pressure (15 to 20 mm Hg). 30 g of reaction product were recovered, the analysis of which by gaseous phase chromatography, infrared chromatography and mass spectroscopy evidenced it to be N-(-meta-trifluoromethylbenzyl)phthalimide.

EXAMPLE 2

Preparation of N-(-meta-trifluoromethylbenzyl)succinimide

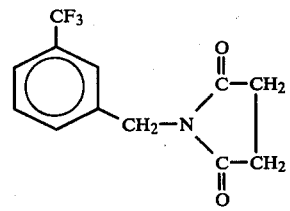

The procedure of Example 1 was repeated, but the reactants were 100 g anhydrous HF (5 moles), 29.2 g trifluoromethylbenzene (0.2 mole) and 30 g (0.23 mole) hydroxymethylsuccinimide.

The heating was at 50° C. for 22 hours.

46.8 g of desired compound were obtained.

EXAMPLE 3

Preparation of N-ortho- and N-(-para-fluorobenzyl)succinimide

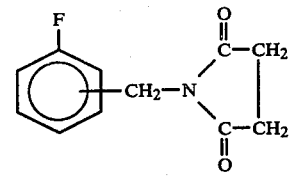

The procedure of Example 1 was again repeated, but the reactants were 100 g anhydrous HF (5 moles), 19.2 g (0.2 mole) fluorobenzene and 30 g (0.23 mole) hydroxymethylsuccinimide.

The reaction was carried out at 50° C. for 4 hours.

40 g of a reaction mixture containing 20% N-(-orthofluorobenzyl)succinimide and 80% N-(-para-fluorobenzyl)succinimide were obtained.

EXAMPLE 4

Preparation of N-ortho- and N-(-para-trifluoromethylthiobenzyl)succinimide

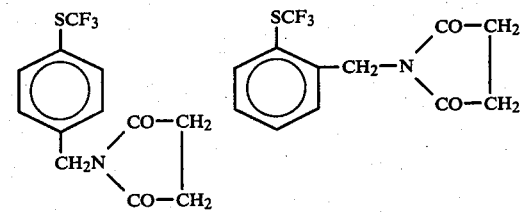

The procedure of Example 1 was again repeated, but the reactants were 100 g anhydrous HF (5 moles), 17.8 g (0.1 mole) trifluoromethylthiobenzene and 12.9 g (0.1 mole) N-hydroxymethylsuccinimide.

The reaction was carried out at 20° C. for 3 hours, 30 minutes.

23.8 g of a reaction mixture containing about 20% N-(-ortho-trifluoromethylthiobenzyl)succinimide and about 80% N-(para-trifluoromethylthiobenzyl)succinimide were obtained.

EXAMPLE 5

Preparation of N-ortho- and N-(para-trifluoromethoxybenzyl)succinimide

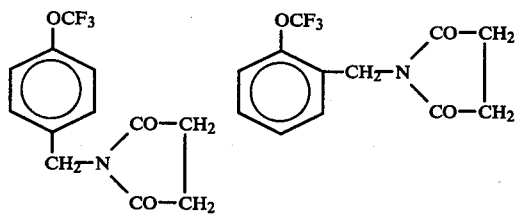

The procedure of Example 1 was again repeated, but the reactants were 100 g anhydrous HF (5 moles), 16.2 g (0.1 mole) trifluoromethoxybenzene and 12.9 g (0.1 mole) N-hydroxymethylsuccinimide.

The reaction was carried out at 10° C. for 3 hours.

18 g of a reaction mixture containing about 15% N-(ortho-trifluoromethoxybenzyl)succinimide and about 85% N-(para-trifluoromethoxybenzyl)succinimide were obtained.

EXAMPLE 6

Preparation of N-(para-trifluoromethylthiobenzyl)phthalimide

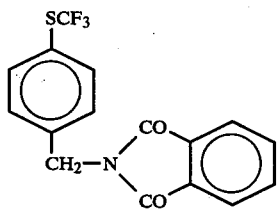

The procedure of Example 1 was again repeated, but the reactants were 50 g anhydrous HF (2.5 moles), 9 g (0.05 moles) trifluoromethylthiobenzene and 9 g (0.05 moles) N-hydroxymethylphthalimide.

The reaction was carried out at 20° C. for 4 hours.

14.7 g N-(para-trifluoromethylthiobenzyl)phthalimide were obtained.

EXAMPLE 7

Preparation of N-ortho- and N-(para-bromobenzyl)glutarimide

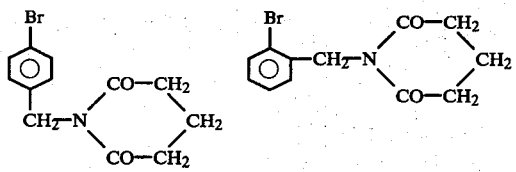

The procedure of Example 1 was again repeated, but the reactants were 100 g anhydrous HF (5 moles), 31.4 g (0.2 mole) bromobenzene and 35.7 g (0.25 mole) N-hydroxymethylglutarimide.

The reaction was carried out at 25° C. for 5 hours.

47.3 g of a mixture of N-(ortho-bromobenzyl)glutarimide and N-(para-bromobenzyl)glutarimide were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an N-benzylimide having the structural formula:

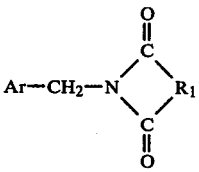

(I)

wherein Ar is a substituted or unsubstituted phenyl radical and $R_1$ is an aliphatic or aromatic hydrocarbon having 1 to 12 carbon atoms, comprising reacting a compound having the structural formula:

ArH   (II)

with a compound having the structural formula:

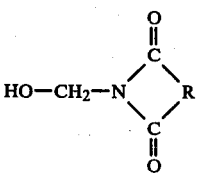

(III)

in the presence of a solvent amount of hydrofluoric acid.

2. The process as defined by claim 1, the hydrofluoric acid being anhydrous hydrofluoric acid.

3. The process as defined by claim 1, the hydrofluoric acid being at a concentration of at least 90%.

4. The process as defined by claim 1, wherein Ar is unsubstituted phenyl.

5. The process as defined by claim 1, wherein Ar is phenyl substituted with at least one of the substituents F, Cl, Br, CN, NO$_2$, NH$_2$, CHO, COOH, COR or COOR, wherein R is alkyl having from 1 to 6 carbon atoms, alkyl or alkoxy having from 1 to 6 carbon atoms, phenyl, phenoxy, CF$_3$, SCF$_3$ and OCF$_3$.

6. The process as defined by claims 4 or 5, wherein $R_1$ is —CH$_2$—CH$_2$—, —CH$_2$—CH$_2$—CH$_2$— or

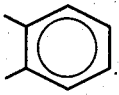

7. The process as defined by claims 4 or 5, the molar ratio of the hydrofluoric acid to the reactant having the Formula (II) ranging from about 5:1 to about 50:1.

8. The process as defined by claim 7, the molar ratio of the reactant having the Formula (II) to the reactant having the Formula (III) ranging from about 0.5:1 to about 2:1.

9. The process as defined by claim 8, the reaction being carried out at a temperature ranging from about 0° C. to 100° C., at about atmospheric pressure.

10. The process as defined by claim 1, for the preparation of one of the N-benzylimides: N-(meta-trifluoromethylbenzyl)phthalimide, N-(meta-bis-trifluoromethylbenzyl)phthalimide, N-(2,4-dichlorobenzyl)phthalimide, N-ortho- and N-(para-trifluoromethoxybenzyl)phthalimide, N-ortho- and N-(para-fluorobenzyl)phthalimide, N-ortho- and N-(para-trifluoromethylthiobenzyl)phthalimide, and the corresponding succinimides and glutarimides.

* * * * *